US009895547B2

(12) United States Patent
Sahin et al.

(10) Patent No.: US 9,895,547 B2
(45) Date of Patent: Feb. 20, 2018

(54) BIOCOMPATIBLE AND IMPLANTABLE OPTICAL CONDUITS

(71) Applicant: New Jersey Institute of Technoloty, Newark, NJ (US)

(72) Inventors: Mesut Sahin, Clifton, NJ (US); Ali Ersen, North Arlington, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 15 days.

(21) Appl. No.: 15/098,497

(22) Filed: Apr. 14, 2016

(65) Prior Publication Data

US 2016/0303384 A1    Oct. 20, 2016

Related U.S. Application Data

(60) Provisional application No. 62/148,152, filed on Apr. 15, 2015.

(51) Int. Cl.
| | | |
|---|---|---|
| *A61N 1/00* | (2006.01) | |
| *A61N 1/378* | (2006.01) | |
| *A61N 1/36* | (2006.01) | |
| *A61N 5/06* | (2006.01) | |
| *A61N 1/372* | (2006.01) | |

(Continued)

(52) U.S. Cl.
CPC ......... *A61N 1/3787* (2013.01); *A61N 1/3605* (2013.01); *A61N 1/37217* (2013.01); *A61N 5/0622* (2013.01); *H02J 50/30* (2016.02); *A61N 2005/063* (2013.01); *A61N 2005/067* (2013.01); *A61N 2005/0612* (2013.01); *A61N 2005/0651* (2013.01)

(58) Field of Classification Search
CPC ............................ A61N 1/3787; A61N 1/3605

USPC .......................................................... 607/61
See application file for complete search history.

(56) References Cited

U.S. PATENT DOCUMENTS

| | | | |
|---|---|---|---|
| 2006/0020239 A1* | 1/2006 | Geiger | A61B 5/0031 604/9 |
| 2006/0030901 A1* | 2/2006 | Quiles | A61N 1/08 607/60 |

OTHER PUBLICATIONS

Unlu, M.S., et al., High-speed Si resonant cavity enhanced photodetectors and arrays. 10 Journal of Vacuum Science & Technology A: Vacuum, Surfaces, and Films, 2004. 22(3): p. 781-787.

(Continued)

*Primary Examiner* — Nadia A Mahmood
(74) *Attorney, Agent, or Firm* — McCarter & English, LLP

(57) ABSTRACT

The present disclosure provides advantageous optical conduit assemblies (e.g., biocompatible and implantable optical conduit assemblies), and related methods of use. More particularly, the present disclosure provides advantageous optical conduit assemblies (e.g., polydimethylsiloxane ("PDMS")-based optical conduit assemblies) configured to power implantable devices (e.g., neural micro-stimulators or deep brain stimulators or the like) or to be used in optogenetic stimulation. In general, the exemplary optical conduit assemblies can be used for applications where energy needs to be transmitted to deep locations inside the body or brain without using electrical wires. Therefore, implantable devices that need to be powered (e.g., neural prosthetics) can be powered from an external light source using an optical conduit and an optical-to-electrical converter (e.g., a photodiode) attached to the end of the optical conduit on the inside.

17 Claims, 13 Drawing Sheets

(51) Int. Cl.
 H02J 50/30 (2016.01)
 A61N 5/067 (2006.01)

(56) References Cited

OTHER PUBLICATIONS

Muller, P., et al., Design and Integration of All-Silicon Fiber-Optic Receivers for Multi-Gigabit Chip-to-Chip Links, in European Solid-State Circuits Conference. 2006:Montreux, Switzerland.

Leblebici, Y, Subthreshold Source-Coupled Circuit Design for Ultra-Low-Power Applications. In Distinguished Lecturer of the IEEE Circuits and Systems Society. 2010-2011.

Abdo et al., Floating light-activated microelectrical stimulators tested in the rat spinal cord. J Neural Eng, 2011. 8(5): p. 056012.

Abdo et al, Intraspinal stimulation with light activated microstimulators. In Neural Engineering (NER), 2011 5th International IEEE/EMBS Conference on. 2011.

Abdo et al., Temperature elevation inside neural tissue illuminated by NIR laser. In Engineering in Medicine and Biology Society,EMBC, 2011 Annual International Conference of the IEEE. 2011.

Freedman, D.S., et al. Addressable floating light activated microelectrical stimulators for wireless neurostimulation. In Neural Engineering (NER), 2011 5th International IEEE/EMBS Conference on. 2011.

Abdo et al., Near-infrared light penetration profile in the rodent brain. J Biomed Opt, 2013. 18(7): p. 075001.

Koklu, G., et al., Characterization of standard CMOS compatible photodiodes and pixels for Lab-on-Chip devices, in IEEE International Sympositum on Circuits and Systems (ISCAS). 2013. p. 1075-1078.

Yucel et al., FEA Modeling of Temperature Elevation in Neural Tissue Illuminated by a Laser: Transient Effects, in 6th Annual International IEEE EMBS Conference on Neural Engineering. 2013, IEEE: San Diego, California. p. 1112-1114.

Ersen et al., Temperature elevation profile inside the rat brain induced by a laser beam. J Biomed Opt, 2014. 19(1): p. 15009.

Ersen, A., et al., Chronic tissue response to untethered microelectrode implants in the rat brain and spinal cord. J Neural Eng, 2015. 12(1): p. 016019.

U.S. Appl. No. 62/148,152, filed Apr. 15, 2015.

\* cited by examiner

BIOCOMPATIBLE AND IMPLANTABLE OPTICAL CONDUITS

CROSS-REFERENCE TO RELATED APPLICATIONS

This application claims the benefit of U.S. Provisional Application entitled "System And Method For Light Conduits Made From Biocompatible Materials For Implantation," which was filed on Apr. 15, 2015, and assigned Ser. No. 62/148,152, the contents of which are herein incorporated by reference in their entirety.

STATEMENT REGARDING FEDERALLY SPONSORED RESEARCH

This invention was made with government support from the National Institutes of Health under grant and/or contract NIBIB R01 EB009100 and NINDS R01 NS0785. The government has certain rights in this invention.

FIELD OF THE DISCLOSURE

The present disclosure relates to optical conduit assemblies (e.g., implantable optical conduit assemblies) and related methods of use and, more particularly, to optical conduit assemblies (e.g., polydimethylsiloxane ("PDMS")-based optical conduit assemblies) configured to power implantable devices (e.g., neural micro-stimulators such as deep brain stimulators or the like) or to be used in optogenetic applications.

BACKGROUND OF THE DISCLOSURE

Micro-stimulation is a powerful tool for restoration of impaired functions in the central and peripheral nervous systems. Microelectrode arrays with conventional fine interconnects have been used in development of neural prosthetics. However, microelectrode implants often fail in long term because of tethering forces of the connecting wires. Also, there is a mechanic stress that occurs at the device-tissue interface because the microelectrode is a rigid body floating in soft tissue and it generally cannot reshape itself to comply with changes in the surrounding tissue. Further, encapsulation inside neural tissue is a major problem, and can result in device failure for chronic implantation.

Thus, an interest exists for improved assemblies configured to power implantable devices without wire attachments (e.g., neural stimulators), and related methods of use. These and other inefficiencies and opportunities for improvement are addressed and/or overcome by the assemblies, systems and methods of the present disclosure.

SUMMARY OF THE DISCLOSURE

The present disclosure provides advantageous optical conduit assemblies (e.g., biocompatible and implantable optical conduit assemblies), and related methods of use. More particularly, the present disclosure provides advantageous optical conduit assemblies (e.g., PDMS-based optical conduit assemblies) configured to power implantable devices (e.g., neural stimulators including deep brain stimulators or the like) or to be used in optogenetic applications.

In general, the exemplary optical conduit assemblies can be used for applications where energy needs to be transmitted to deep locations inside the body or brain without using electrical wires. Therefore, implantable devices that need to be powered (e.g., neural prosthetics) can be powered from an external light source using an optical conduit and an optical-to-electrical converter (e.g., a photodiode) attached to the optical conduit (e.g., attached to the distal tip of the optical conduit on the inside end of the optical conduit).

In neural prosthetics such as chronically implanted micro-stimulators, the present disclosure advantageously provides for flexible, biocompatible, untethered devices. These stimulators can require delivery of optical energy to the site of implant, which may be several centimeters away from the skin or an extracorporeal light source.

In general, optical conduits (or waveguides) are constructs of translucent material that can be designed to collect and transmit light. The use of optical conduits particularly in the area of neural engineering or neural prosthetics is currently non-existent.

For example, in those applications where the targeted implant sites are away from a bony structure like the skull or vertebrae, optical energy harvested subcutaneously needs to be transferred to the location of the implant with sufficient efficiency. This optical harvesting and transfer system should be robust enough to survive the mechanical challenges of continuously moving tissues around, soft enough not to damage other neural tissues in the path, and biocompatible. Furthermore, implantable electronics can impose stringent design criteria in terms of size and power and require hermetic sealing that should last the lifetime of the implant.

The present disclosure provides for an optical conduit assembly including an optical conduit configured to be positioned in a first desired anatomical location, the optical conduit configured to wirelessly transmit optical energy to an implantable device; a light source configured to deliver optical energy to the optical conduit; wherein after the light source delivers optical energy to the optical conduit, the optical conduit wirelessly transmits optical energy to the implantable device, the implantable device positioned in a second desired anatomical location.

The present disclosure also provides for an optical conduit assembly wherein the optical conduit is a PDMS-based optical conduit. The present disclosure also provides for an optical conduit assembly wherein the implantable device is an untethered neural micro-stimulator or a neural prosthetic.

The present disclosure also provides for an optical conduit assembly wherein the first desired anatomical location includes the epidermis, and wherein the second desired anatomical location is a deep location inside the body or brain.

The present disclosure also provides for an optical conduit assembly wherein the light source is an external laser diode. The present disclosure also provides for an optical conduit assembly wherein the optical conduit includes an optical-to electrical converter attached to a distal tip of the optical conduit. The present disclosure also provides for an optical conduit assembly wherein the optical-to electrical converter is a photodiode.

The present disclosure also provides for an optical conduit assembly wherein the optical conduit includes at least one curved section. The present disclosure also provides for an optical conduit assembly wherein the implantable device includes an optical-to electrical converter.

The present disclosure also provides for a method to power implantable devices including providing an optical conduit configured to wirelessly transmit optical energy to an implantable device; positioning the optical conduit in a first desired anatomical location; providing a light source configured to deliver optical energy to the optical conduit;

positioning an implantable device in a second desired anatomical location; delivering optical energy to the optical conduit via the light source so that the optical conduit wirelessly transmits optical energy to the implantable device.

The present disclosure also provides for a method to power implantable devices wherein the optical conduit is a PDMS-based optical conduit. The present disclosure also provides for a method to power implantable devices wherein the untethered implantable device is an untethered neural micro-stimulator or a neural prosthetic.

The present disclosure also provides for a method to power implantable devices wherein the first desired anatomical location includes the epidermis, and wherein the second desired anatomical location is a deep location inside the body or brain.

The present disclosure also provides for a method to power implantable devices wherein the light source is an external laser diode. The present disclosure also provides for a method to power implantable devices wherein the optical conduit includes an optical-to electrical converter attached to a distal tip of the optical conduit. The present disclosure also provides for a method to power implantable devices wherein the optical-to electrical converter is a photodiode.

The present disclosure also provides for a method to power implantable devices wherein the optical conduit includes at least one curved section. The present disclosure also provides for a method to power implantable devices wherein the implantable device includes an optical-to electrical converter.

The present disclosure also provides for an optical conduit system including a plurality of an optical conduits configured to be positioned in a first desired anatomical location; a plurality of light sources, each light source configured to deliver optical energy to a respective optical conduit of the plurality of optical conduits; a plurality of implantable devices configured to be positioned in a second desired anatomical location; wherein after each light source delivers optical energy to its respective optical conduit of the plurality of optical conduits, each optical conduit wirelessly transmits optical energy to a respective implantable device of the plurality of implantable devices.

The present disclosure also provides for an optical conduit system further including a substrate having a plurality of holes, each hole configured and dimensioned to house an end of one respective optical conduit of the plurality of optical conduits.

Any combination or permutation of embodiments is envisioned. Additional advantageous features, functions and applications of the disclosed assemblies, systems and methods of the present disclosure will be apparent from the description which follows, particularly when read in conjunction with the appended figures. All references listed in this disclosure are hereby incorporated by reference in their entireties.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the scope of the present disclosure. To assist those of ordinary skill in the art in making and using the disclosed assemblies, systems and methods, reference is made to the appended figures, wherein.

DETAILED DESCRIPTION OF DISCLOSURE

The exemplary embodiments disclosed herein are illustrative of advantageous assemblies to power implantable devices (e.g., neural micro-stimulators), and systems of the present disclosure and methods/techniques thereof. It should be understood, however, that the disclosed embodiments are merely exemplary of the present disclosure, which may be embodied in various forms. Therefore, details disclosed herein with reference to exemplary assemblies/fabrication methods and associated processes/techniques of assembly and use are not to be interpreted as limiting, but merely as the basis for teaching one skilled in the art how to make and use the advantageous assemblies/systems and/or alternative assemblies/systems of the present disclosure.

The present disclosure provides advantageous optical conduit assemblies (e.g., biocompatible, implantable optical conduit assemblies), and related methods of use. In particular, the present disclosure provides advantageous optical conduit assemblies (e.g., polydimethylsiloxane (PDMS)-based optical conduit assemblies) configured to power implantable devices (e.g., neural micro-stimulators including deep brain stimulators or the like) or to be used in optogenetic applications.

In exemplary embodiments, the present disclosure provides optical conduit assemblies that can be used for applications where energy needs to be transmitted to deep locations inside the body or brain without using electrical wires. Thus, certain implantable devices (e.g., neural prosthetics) can be powered from an external light source using an optical conduit and an optical-to-electrical converter (e.g., a photodiode) attached to the optical conduit (e.g., attached to the tip of the optical conduit on the inside end of the optical conduit).

Current practice provides that microelectrode implants often fail in long term because of tethering forces of the connecting wires, and there can be a mechanic stress that occurs at the device-tissue interface because the microelectrode is a rigid body floating in soft tissue and it generally cannot reshape itself to comply with changes in the surrounding tissue. Further, encapsulation inside neural tissue is a major problem, and can result in device failure for chronic implantation.

In exemplary embodiments, the present disclosure advantageously provides for optical conduit assemblies that can be used for applications where energy needs to be transmitted to deep locations inside the body/brain without using electrical wires, which allows certain implantable devices (e.g., neural prosthetics) to be powered from an external light source, thereby providing a significant operational, commercial and manufacturing advantage as a result.

Figure 1:
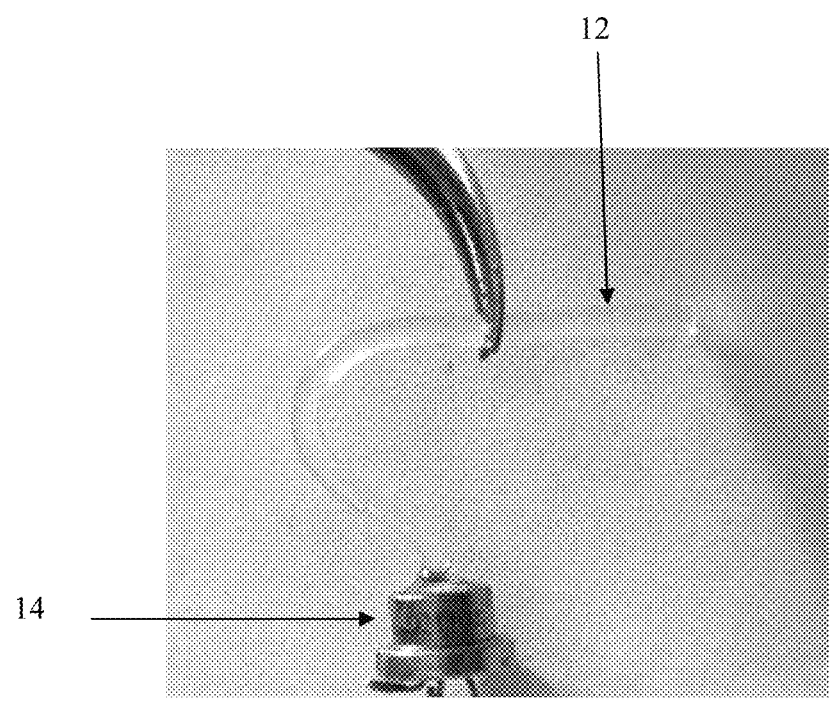
FIG. 1 is an image showing a polydimethylsiloxane (PDMS)-based light conduit attached to a 5 mW red laser diode; light comes from the other end of this 4.2 cm long conduit with minimal loss despite significant curvature.

A biocompatible material that is commonly used as a part of an implantable device is polydimethylsiloxane (PDMS), or commonly known as silicone rubber. Some implantable devices use PDMS as a coating material around the wires and connectors because it is a soft and flexible material and provides insulation from the harmful biological environment inside the body. Light at visible and near infrared wavelengths attenuates going through PDMS partially, however, substantial levels of transmission can be obtained in short distances using an optically clear PDMS optical conduit 12 (FIG. 1). The refractory index of PDMS can be adjusted within a range by mixing it in different ratios, which may be necessary to fabricate an optical conduit that can contain light inside and to minimize the light energy escaping through the walls. FIG. 1 is an image showing a polydimethylsiloxane (PDMS)-based light conduit 12 attached to a light source 14 (e.g., a 5 mW red laser diode 14); light comes from the other end of this 4.2 cm long conduit 12 with minimal loss despite significant curvature.

One embodiment of the present disclosure utilizes optical conduits in order to transfer energy to prosthetic devices implanted deep inside the body (e.g., inside the skull, abdomen, or other locations/cavities in a body/organism). Some current approaches use electromagnetic waves to power electronics implanted as a part of a neuro-prosthetic device. However, electromagnetic waves attenuate substantially by depth, the external coils are bulky, and recovery of the electromagnetic energy by the implant can require another coil and complex electronics.

Figure 2:
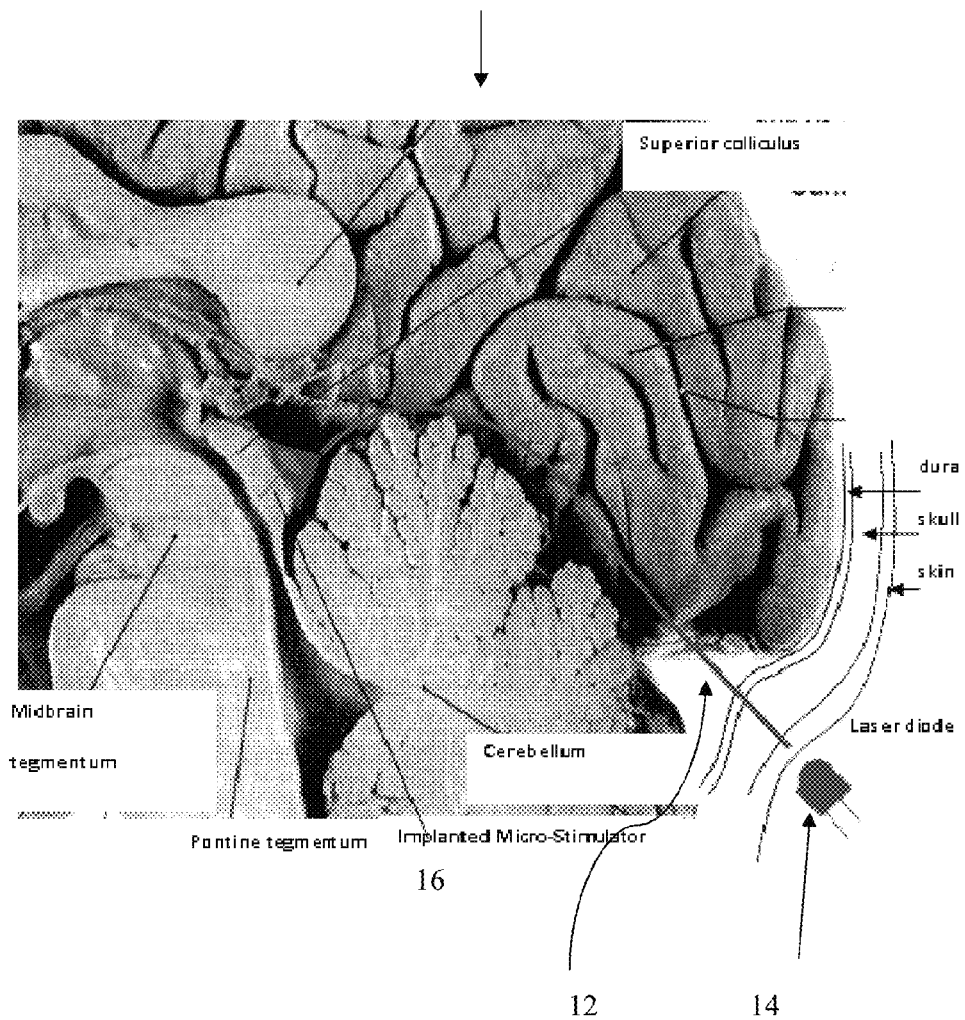
FIG. 2 shows a targeted implant site for untethered micro-stimulators in the inferior colliculus and the light conduit for transcutaneous delivery of stimulus energy.

The optical approach of the present disclosure advantageously mitigates these problems. In one embodiment of the present disclosure and as shown in FIG. 2, the light energy is sent through the skin and collected with a light conduit 12 that transfers the energy to a location where it converts to electrical current using a small photodiode. This embodiment provides a more efficient means of transcutaneous energy transfer, and also eliminates the wire breakage problem that often limits the lifetime of a conventional implant. Even if the conventional metal wires are flexible and strong, these conventional metal wires can last only for a limited time inside the body due to mechanical stress and constantly moving surrounding tissue. As a result, conventional implant wires typically cannot go through moving locations in the body like the joints, groin area, neck, etc.

In another embodiment of the present disclosure, biocompatible optical conduits utilizing materials such as PDMS optical conduits can be used in optogenetics (a technique that is utilized in neurosciences for stimulating neural cells using light). Optical guides of this embodiment can transmit the commonly used wavelengths (blue) and provide soft, biocompatible, and durable probes to be used by researchers in lab animals or the like. The current conventional probes are rigid and thus induce too much injury on the neural structures that are being investigated around the probe.

By powering an implantable device 16 (e.g., a micro stimulator 16) transcutaneously, and thereby removing the implantable electronics, a major source of failure is eliminated with exemplary embodiments of the present disclosure. Also, in some embodiments, pulse parameter control from the external electronics is gained. Thus, the optical transcutaneous energy transfer paradigm can be extended to many other implantable neural prosthetics to deliver energy where it is needed deep inside the tissue without using interconnecting wires.

In an embodiment of the present disclosure, the conduit 12 design is discussed below. An optical fiber was fabricated using commercial PDMS with a refractory index of approximately 1.54 for the core, and approximately 1.46 for the cladding. Both materials had an attenuation coefficient (insertion loss) of less than about 0.4 dB per cm. Attenuation of the material is very similar at red and near infrared wavelengths. An important design issue of this exemplary embodiment was to focus the external light beam into this optical conduit 12 to obtain maximum efficiency. In yet further embodiments, square cross-section conduits that allowed one to use standard photolithography methods for high accuracy and reproducibility of results were also embraced.

The external optical source 14 (e.g., high power laser diode array) and electronic driver circuit that can produce very short current pulses was utilized in an embodiment. Embodiments of the present disclosure achieved about a 25% efficiency over a distance of around 10 cm. Further embodiments achieved at least about 50% efficiency over a distance of around 10 cm, which corresponds to about 4 dB for 10 cm (e.g., 2.5 times or 60%).

In a tested embodiment, the optical conduit's large end was placed against a skin sample extracted from a swine freshly after termination and not frozen. The muscle and subcutaneous fat was removed. Different samples from different animals were relied upon for obtaining a range of skin thicknesses from about 2 mm to about 10 mm. The optical source was placed against the skin after shaving and removing the fine fur with depilatory cream. The light emanating from the other end of the conduit was collected and measured with an optical power measurement device. The optical conduit wraps around a cylindrical object with varying diameters (around 1 to around 5 cm) to simulate reshaping of the conduit that takes place in a chronic implant. The length of the conduit was varied by cutting 0.5 cm of its length at a time from the end where the light exits. The attenuation of light was plotted as a function of conduit length, bending diameter, and the skin thickness. Finally, the tip of the optical conduit was placed at about 3 cm from a photodiode that had the same light receiving window size as the pin-FLAMES ("Floating Light Activated Micro-Electrical Stimulators"). The total energy transfer efficiency from the external light source, through the skin and conduit, and the output of the photodiode was calculated to help estimate real case scenario of chronic implantation.

One example for a biocompatible substance to be used in certain embodiments of the present disclosure is PDMS. In general, PDMS has excellent properties being a compliant material with mechanical impedance close to soft tissue, relatively less optical attenuation in wide light spectrum and is biocompatible.

The core and cladding of such embodiment were fabricated using PDMS with difference refractory indices; one with a relatively higher index for the core with and another for cladding. The conduit was coupled to a red laser diode and the light exiting from the smaller end was collected with a photodiode for measurements of attenuation at various lengths by cutting the conduit. The results demonstrated that the conduit had a good confinement of red light and relatively low attenuation of approximately 0.4-0.5 dB/cm in straight positioning. Attenuation under bent conditions such as 90, 180, 270 and 360 degrees were studied to evaluate transmission efficiency for cases where the conduit will be making curves in order to reach deep structures in the central nervous system ("CNS").

Figure 3:
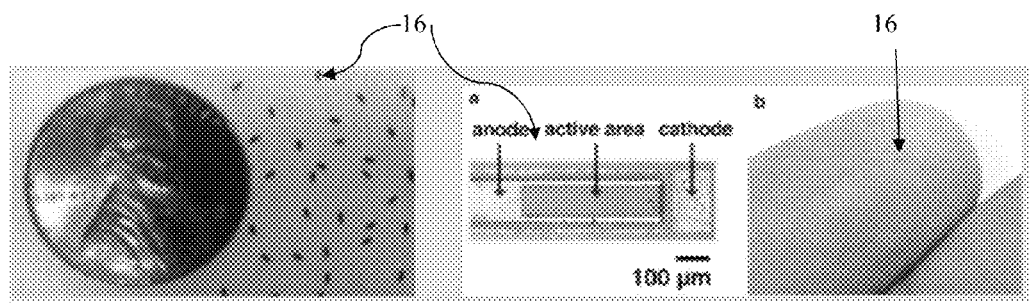
FIG. 3 shows untethered light-activated neural micro-stimulators.
Figure 4:
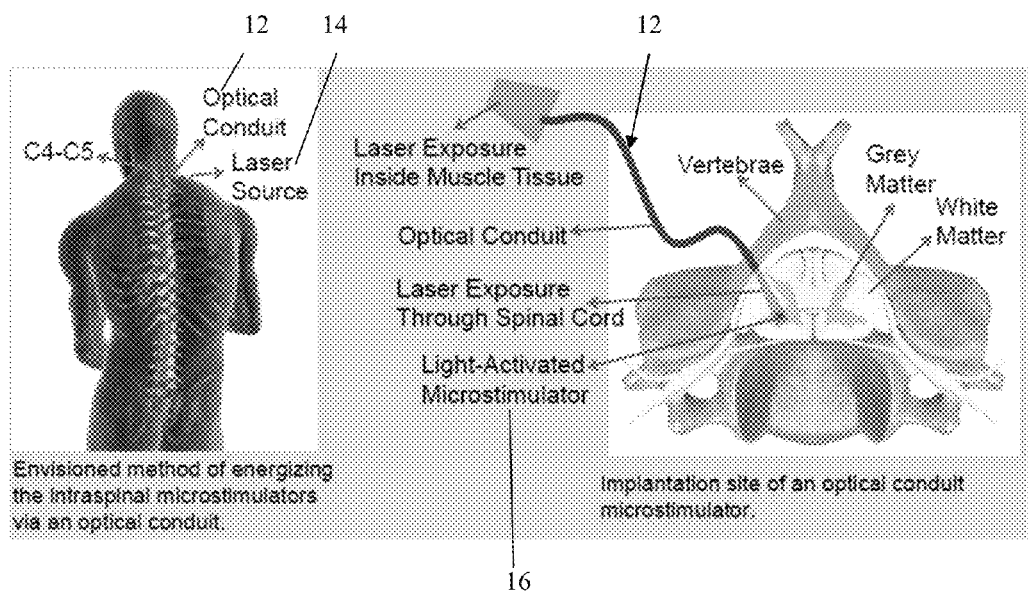
FIG. 4 shows an untethered light activated stimulation system.

The micro-stimulator 16 of one embodiment was implanted into the neural tissue at the targeted site of the CNS, typically a few millimeters below the pial surface. The laser source 14 and control electronics of such embodiment were implanted at a distant site that was convenient for transcutaneous charging of batteries and programming of the pulse parameters. An optical conduit 12 was used to transfer the laser pulses near the micro stimulator 14 to activate it. The tip of the optical conduit 12 was located just above the micro-stimulator 16, but outside the dura matter, and was inserted through a hole into the skull or vertebrae. Therefore, the distance that the laser beam had to travel was only in the order of a few millimeters (about 1 to about 20 mm) into the neural tissue above the micro stimulator 16 (FIGS. 3-4).

As noted, the core and cladding for an exemplary embodiment was fabricated using PDMS with different refractory indices ("RI"); one with a relatively higher index for the core with RI=1.55 (Dow Corning OE-6550), and another with RI=1.41 for cladding (Dow Corning Slygard 184).

Figure 5:
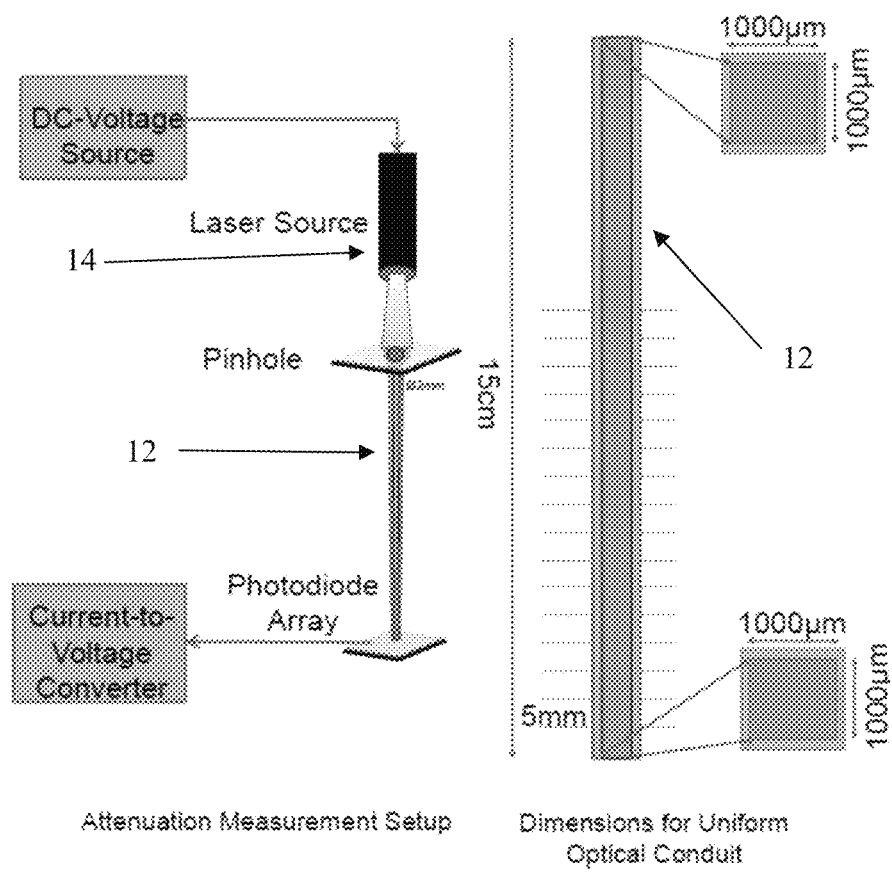
FIG. 5 shows conduit attenuation measurement setups.

The cladded conduit 12 of an embodiment was coupled to a red laser diode 14 (Flexipoint Laser Diode Module, 655 nm, 4.9 mW), and the light exiting from the smaller end was collected with a photodiode (Thorlabs, Silicon Photodiode, 10 mm>10 mm active area) for measurements of attenuation at various lengths by cutting around 5 mm of the conduit each time (FIG. 5).

Figure 6:
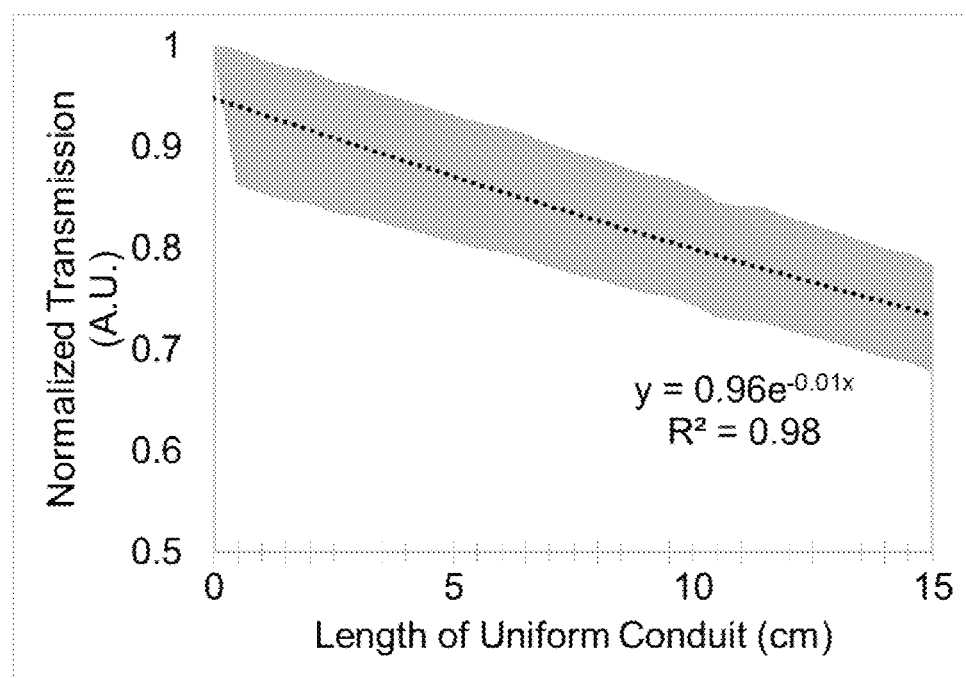
FIG. 6 shows normalized transmission of uniform PDMS conduits with respect to conduit length using a red laser source ($\lambda$=655 nm)

FIG. 6 shows normalized transmission of uniform PDMS conduits with respect to conduit length using a red laser source ($\lambda$=655 nm). The gray shade shows the plus/minus standard deviation, and the dash line is an exponential fitted ($R^2$=0.98) to the mean of measurements at various lengths obtained by cutting 5 mm of the conduit each time. The transmitted light was collected by a photodiode at the end of the conduit.

Figure 7:
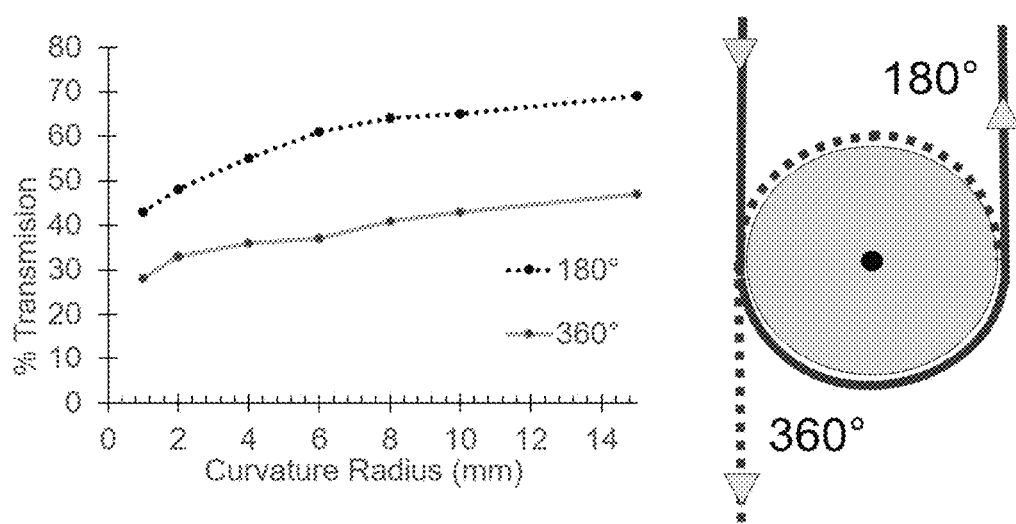
FIG. 7 shows percentage optical transmission though the PDMS conduits at 180° and 360° bending angles with radii of curvature varied between 1-15 mm.

FIG. 7 shows percentage optical transmission though the PDMS conduits at 180° and 360° bending angles with radii of curvature varied between 1 to 15 mm.

In exemplary embodiments, the uniform optical conduit had a good confinement of red light ($\lambda$=655 nm) and relatively low attenuation of approximately 0.46 plus/minus 0.03 dB/cm in straight positioning.

Attenuation under bent conditions at 180 and 360 degrees with 8 mm radius were evaluated around 63% and 40% transmission percentage respectively, for cases where the conduit will be making curves in order to reach deep structures in the CNS. These findings indicate that PDMS-based conduits can be used in powering intra-spinal micro-stimulators.

Because the OE-6550 and Slygard184 have relatively flat transmission spectra across the visible spectrum, these flexible conduits can deliver light into depths of neural tissue within a wide range of wavelengths including those used in opto-genetic neural stimulation. Consequently, PDMS-based optical conduits provide a step towards the development of biocompatible, flexible and untethered optoelectronic neuro-prosthetics.

The present disclosure will be further described with respect to the following examples; however, the scope of the disclosure is not limited thereby. The following examples illustrate the advantageous optical conduit assemblies (e.g., PDMS-based optical conduit assemblies) configured to power implantable devices (e.g., untethered neural micro-stimulators) or the like, and related methods of use.

EXAMPLE 1:

Multi-electrode arrays ("MEAs") have employed technologies to produce fine 2D and 3D constructs by attempting to optimize the electrode mechanical properties between flexibility and robustness. These MEAs are being used as a research tool in animal models and in some clinical trials. In general, MEAs are well suited for cortical implants where the targeted neural structures are beneath the skull and where they experience relatively small movements. Typically, those arrays cease to function after a few years due to neural tissue scarring that forms around the electrode shanks, and they have to be explanted at the end of the study from the subject. The tethering of the inter-connecting wires or ribbon cables is believed to be the major cause of the on-going tissue response in long-term implants. The rigidity of the shanks and the substrate exacerbate the mechanical stress induced by the tethers.

Some micro-stimulation ideas in the CNS cannot be tested with chronic implants in animal models because of the challenge presented by the implant location that experiences high levels of motion and they are further away from a stable bony structure like the skull. Some of those implant locations are in the midbrain, the brain stem and the spinal cord. Macro electrodes that are commonly used for deep brain stimulation generally do not provide a solution since the targeted neural structures are much smaller than the electrode contacts and selective activation is typically required for functional results in these applications.

One such application is the auditory midbrain implant ("AMI") that is currently being pursued with clinical trials in the USA and Europe. A primary roadblock in this approach is the lack of spatial selectivity with the macro electrodes approved for implantation. A targeted population for AMI is people with hearing disability due to a compromised auditory nerve who cannot benefit from a cochlear implant. The site of stimulation is the inferior colliculus in the midbrain that is approachable with a dorsal craniotomy and by reaching behind the cerebellum. The inferior colliculus is near the surface of the pia mater, however, at a significant distance from the dura and the skull (FIG. 2). A 3D multi-electrode array implant with tethers may be mechanically highly unstable and thus induce substantial damage to the targeted neural structures to be micro-stimulated. Wires or a ribbon cable are not likely to survive for a very long time due to movement of the neck and the midbrain with respect to the skull. The present disclosure proposes to use wireless multi-contact floating devices for this application towards a clinical implementation. Other potential applications in the spinal cord and the brain stem will be discussed as well.

In order to achieve the high level of spatial selectivity required in most CNS applications, microelectrode arrays with penetrating shanks have been developed. A number of groups have been working successfully towards the development of batch-processable micro-scale array electrodes, mostly using metal or semiconductor materials that have a Young modulus that is several orders of magnitude higher than the neural tissue. The substrate that holds individual shanks together (e.g., silicon, ceramic, etc.) further increases the size of the rigid body by forming a 3D structure that is moving inside a volume of tissue that is very soft and viscoelastic. As such, mechanical perturbation (blood flow pulsation, respiration, whole body acceleration, gravity, etc.) that moves the tissue causes frictional forces around the electrode shanks and scarring due the mechanical mismatch between the soft tissue and a rigid 3D electrode array. The substrates are usually flat and rigid and do not conform to the brain surface and tend to cause damage to the most superficial few hundred microns of the neural tissue in long term implants.

An intuitive way of minimizing the tissue reaction and scarring is to eliminate the tethering forces by removing the inter-connecting wires and transmit the stimulation energy to each electrode contact wirelessly. In this case, the electrode becomes a floating device both mechanically and electrically. Eliminating the interconnecting wires will also improve device longevity by solving the wire breakage problem, which is usually the most common source of failure in implanted neural electrodes.

In general, "Floating Light Activated Micro-Electrical Stimulators" (FLAMESs) are sub-millimeter-size, wireless stimulators that are optically activated by a laser beam that travels through the neural tissue. In one version, the device did not contain active electronics or charge storage, but only passive photodiodes to harvest optical energy. The device instantaneously converts the photons into an electric current that flows through the tissue and thereby activates the neural structures around the device in a volume of about its own size. These floating single channel micro-stimulators were developed for wireless stimulation.

Currently, many neural stimulation projects are held back at the pre-clinical testing phase because of the high risk of neural insult involved with 3D micro-electrode array implants. This is a greater problem in highly mobile parts of the CNS such as the midbrain, the brain stem, and the spinal cord. The availability of such electrode technology will enable translation of several neuroprosthetic ideas into clinical trials. Some innovational aspects of such embodiments can be itemized as follows: (i) an optically powered electrode array with optically controlled stimulation parameters, (ii) a PDMS light conduit that provides virtually tether-free, transcutaneous link, and/or (iii) a novel neuro-prosthetic application, the AMI, that can truly benefit from a floating micro electrode for improved functionality.

Figure 8:
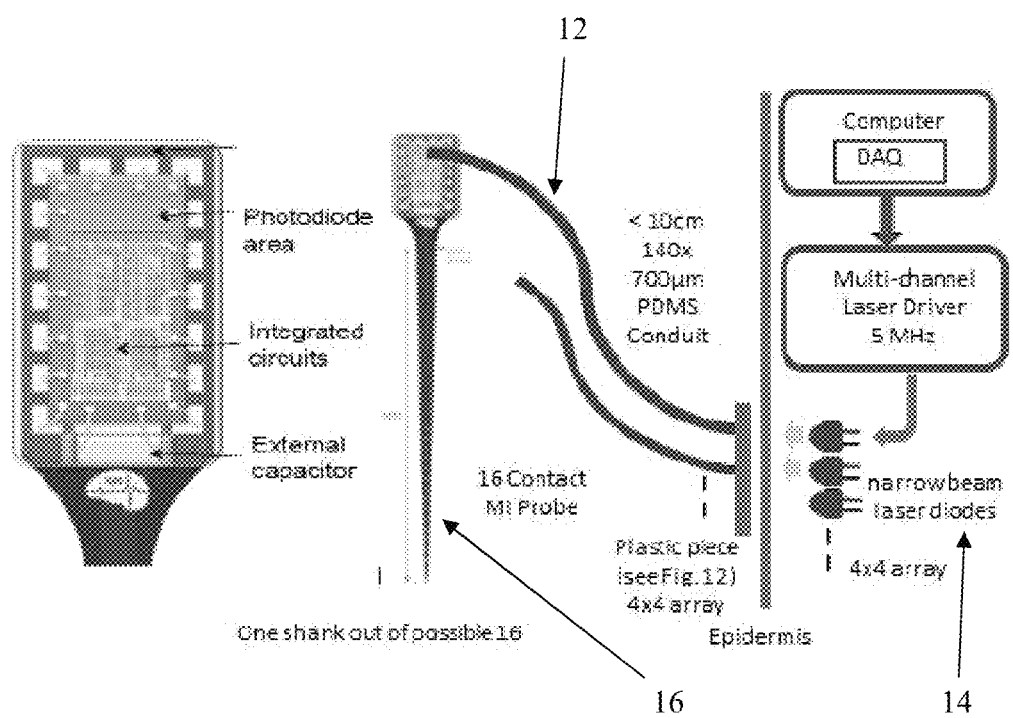
FIG. 8 shows a block diagram of an exemplary system—each electrode shank is connected to a flat profile, thin, PDMS optical conduit aligned with an external semiconductor laser source across the epidermis—see FIG. 10 for the alignment of external laser sources.
Figure 9:
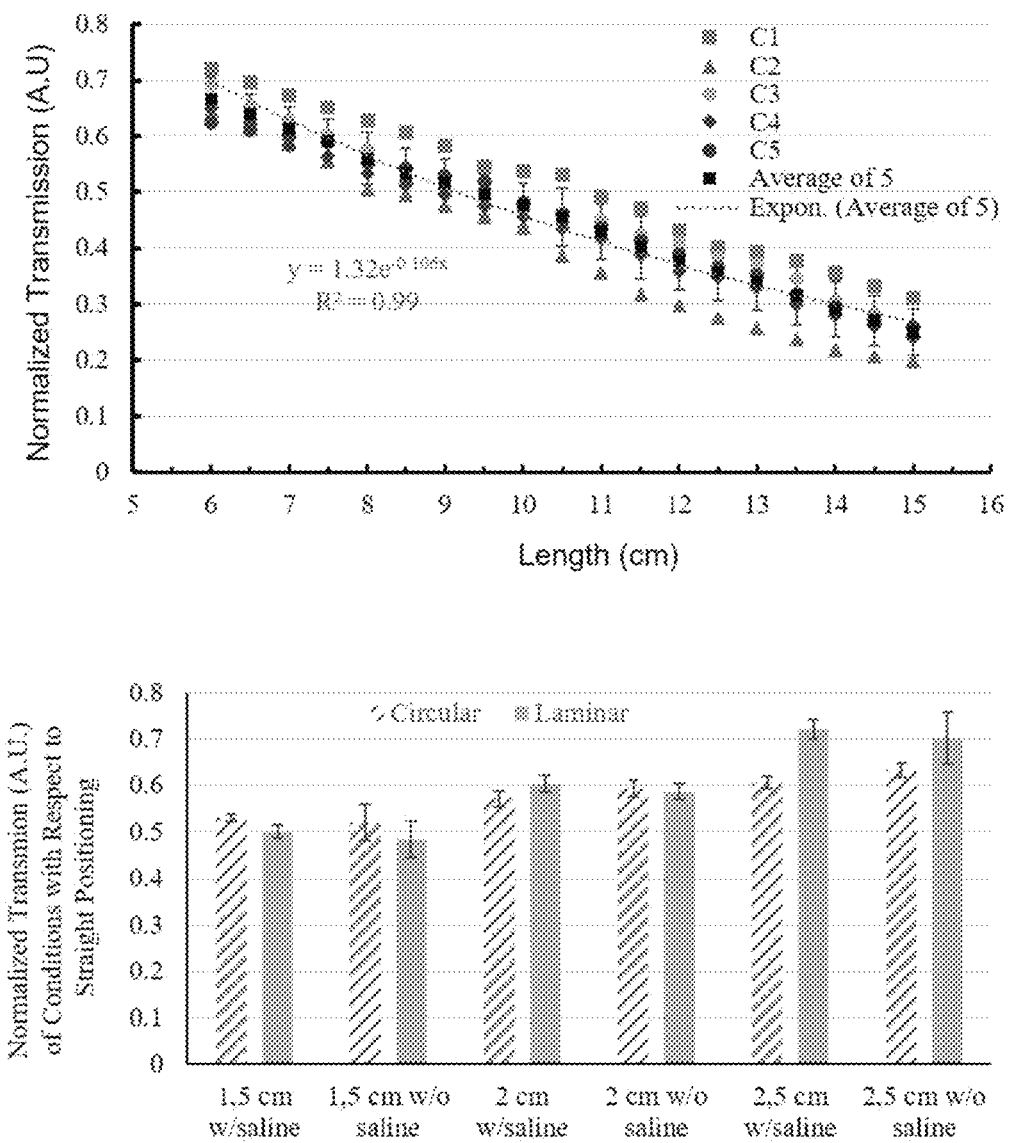
FIG. 9 shows in Top Section: normalized transmission profiles as a function of the cylindrical conduit length; Grey square, grey triangle, grey circle and black diamond dots represent different individual conduit samples; Black squares are the average of the transmission from the five conduits, plus/minus 1 standard deviation is shown in gray; Grey dash line is an exponential curve fit (correlation 0.99) with a single exponent; Bottom Section: normalized transmission of cylindrical and laminar conduits in saline for the length of 12.5 cm as a function of the radius of curvature; Striped bars represent the cylindrical design and solid bars are the laminar one; plus/minus 1 standard deviation of five conduits are shown in black whiskers; Curvature radius set to 1.5 cm, 2 cm, and 2.5 cm are shown for each conduit design.

Block Diagram of The Proposed System:

An exemplary optical conduit assembly 10 includes multiple shank electrodes 16 implanted in the midbrain and connected to individual optical conduits 12 that trace back to a subcutaneous region behind the ears similar to a cochlear implant (FIG. 2). An external array of laser diodes 14 will generate and send the optical pulse patterns through a thin layer of skin and the corresponding optical conduit 12 will transmit the light energy both to power the electronics on the electrode shank 16 and address selected contacts (FIG. 8).

Each multi-contact shank electrode 16, its optical conduit 12, and an external laser diode 14 make up a separate channel with dedicated external control electronics. The number of channels will depend on the application. The speed of transmission is that of an optical communication, which can be in the GHz range if needed. Thus, the stimulus pulses can be delivered at very high rates, including the addressing time that is needed between pulses for selecting different contacts.

Targeted Application: Auditory Brainstem (ABI) and Midbrain Implants (AMI):

In general, Cochlear implants ("CI") are very successful neural prosthetic devices. They have been implanted in more than 320,000 individuals, many of whom are infants that are less than a year old. The CI is typically not an option for those without a functional auditory nerve or an implantable cochlea. As an alternative, stimulation of the brain stem has been pursued in the USA and Europe. At least 1,000 auditory brainstem implants ("ABI") have been implanted in people with neurofibromatosis Type 2, who usually develop bilateral neural deafness due to the growth or surgical removal of bilateral acoustic neuromas and are unable to benefit from cochlear implants. The ABI has shown improvements generally limited to environmental awareness and lip-reading capabilities. Surprisingly, some non-tumor patients (those with nerve avulsion/aplasia, cochlear ossification, etc.) implanted with ABI have achieved open-set speech perception without lip-reading. This suggests that the limited success with the brainstem implants may be due to the damage associated with the removal of the tumor around the cochlear nucleus.

Researchers have proposed that the stimulation of inferior colliculus may be a better alternative because it is proximal to the cochlear nucleus and intact in the neurofibromatosis Type 2 patients. An auditory midbrain implant ("AMI") has been developed that stimulates the central nucleus of the inferior colliculus ("ICC"), which is surgically accessible through a posterior craniotomy and the central nucleus has a tonotopic organization. ICC stimulation also provides lower thresholds, greater dynamic ranges, and more localized frequency-specific activation than cochlear stimulation, which suggests that the midbrain implants may perform better than the cochlear implants. Researchers have tested the feasibility and safety of electrode implants in the cat midbrain, an animal model selected because of similarities in the cytoarchitecture and size of its inferior colliculus to that of human. The electrode array used in these tests was 6.4 mm in length and around 0.4 mm in diameter, and had 20 circular contacts with 126,000 $\mu m^2$ surface area. Nevertheless, when macro electrodes with millimeter dimensions are used in the CNS, such as these by Cochlear Ltd and the DBS electrodes, the chronic tissue response is expected to be low due to the stability of the tissue interface provided by the large size of the array. However, such macro-electrodes cannot generate selective activation of small neuronal networks in order to take advantage of the high level of tonotopic organization in the ICC. Recent studies with micro electrodes suggest that multi-point stimulation within isofrequency laminae of the ICC has a potential to improve speech perception. The micro-electrode arrays with interconnecting wires, on the other hand, may be much less stable due to the tethering forces of the interconnecting wires, which will induce larger displacements of the arrays inside the tissue, and cause significant scar formation and loss of function.

Therefore, the AMI is an ideal application that can benefit from the floating micro-stimulation devices provided for by the present disclosure. Many neural prosthetic ideas dealing with micro stimulation of the midbrain, brain stem or spinal cord are potential applications for pin-FLAMES where the electrodes are subject to extensive amount of motion.

Figure 10:
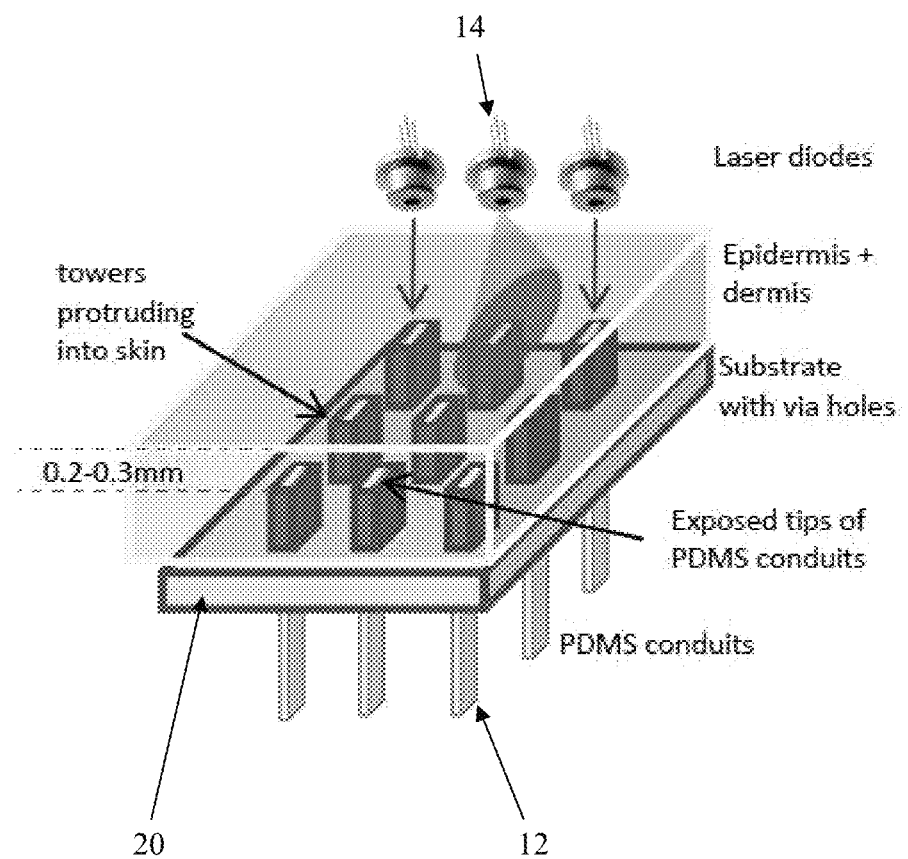
FIG. 10 shows the alignment of PDMS conduits with (external) laser sources using a plastic substrate with protruding towers into the skin to hold the tips of PDMS conduits near epidermis.

External Laser Source:

In exemplary embodiments, each electrode shank 16 may have its dedicated optical conduit 12 (FIG. 10) and an external semiconductor laser diode 14 configured as a matrix with around 5 mm separations, and an electronic driver. FIG. 10 shows the alignment of PDMS conduits 12 with (external) laser sources 14 using a plastic substrate 20 with protruding towers into the skin to hold the tips of PDMS conduits 12 near epidermis. Each diode laser 14 will generate a 20 mW beam in an oval shape profile (e.g., to match the shape of the optical conduit) with about 5 $mm^2$ footprint on the epidermis (20 mW/5 $mm^2$=400 m/$cm^2$). Many semiconductor lasers with longitudinal beam profiles are commercially available to meet these requirements. The choice of wavelength typically is not critical within the 700 to 900 nm band since the attenuation of epidermis is not strongly dependent on wavelength within this optical window. In certain embodiments, the number of laser diodes 14 may be the same as the number of electrode shanks 16 implanted in a given application. The skin area illuminated by each laser beam may be larger than the tip size of the optical conduit 12 to avoid problems due to misalignment. However, the power density in the center of the beam will not exceed the maximum permissible exposure ("MPE") dictated by American National Standard ("ANSI") Z136.1.

EXAMPLE 2:

A PDMS-Based Optical Waveguide for Transcutaneous Powering of Microelectrode Arrays Implantable microelectrode arrays ("MEAs") usually have on-site electronics that need to be powered, both in neural recording and stimulation applications. Interconnecting wires between implanted electrodes and the outside world constitute a major source of complications. One exemplary solution to this tethering problem is to provide a light waveguide that can collect the optical power transcutaneously and transmit it to the microelectrode array, where it is converted to an electric current. A PDMS-based waveguide was fabricated and its attenuation was found to be 0.36 dB/cm in vitro. The skin flap of the thenar web space in the hand was used to test the photon collection efficiency of the waveguide in diffused light. The efficiency of the waveguide alone was 44 plus/minus 11% (mean plus/minus std) as measured in 13 subjects with different skin pigmentations, excluding the attenuation within the thenar skin. These preliminary results suggest that a PDMS waveguide may collect and deliver optical power with sufficient efficiencies into the depths of neural tissue. An exemplary optical powering scheme can solve the breakage problems associated with metal interconnecting wires.

Neural electrodes have employed state-of-the-art technologies to produce fine 2D and 3D constructs for selective neural stimulation and neural activity recording in the central nervous system ("CNS"). So far these electrode arrays are mostly tethered to the outside electronics via fine metal wires. The brain continuously moving inside the skull as a viscoelastic structure causes at least two fundamental problems that are at a trade-off with each other. First, the shear forces generated at the tissue/electrode interfaces increase with the thickness of the wires and the ever increasing number of channels and cause a chronic scar tissue formation around the electrode. Second, the lifetime of the wires is severely limited by the continuous movement of the electrodes and wire breakage becomes a serious issue as they are made thinner to minimize the tethering forces. Unfortunately, conventionally there are no electrically conductive, biologically inert materials that can provide a highly flexible and yet durable interconnection and thus alleviate both problems at the same time.

With wireless powering and signal telemetry, the electrode arrays can float inside the neural tissue and both the glial scar formation and the wire breakage problems are solved together. To this end, other forms of energy transmission can be considered to power the implants, such as optical, electromagnetic, or acoustic. Optical form of energy has a particular advantage that it can be guided and transmitted through an optical fiber, unlike the latter two. A glass or plastic optical fiber perhaps is not very different from a metal wire in regards to its flexibility and durability inside a viscoelastic medium. However, highly flexible and optically transparent materials like the PDMS can be considered for power delivery to neural implants. The PDMS is also highly durable under bending forces and biocompatible for chronic implants. Currently, the usage of PDMS waveguides in powering implantable electronics is non-existent in literature.

The amount of energy that can be delivered through a PDMS-based waveguide is limited only by the maximum permissible exposure ("MPE") of light on the skin. This value is regulated by American National Standard ("ANSI") Z136.1 and given as approximately 400 mW/$cm^2$. Since the MPE limits the amount of light power per unit area of the skin, what is needed to transmit more power is to increase the cross-sectional area of the waveguide. Then the trade-off becomes that of one between the thickness of the optical waveguide and the maximum power that can be delivered, where thicker waveguides will obviously be less flexible. A significant relief to this equation comes from the fact that the Young's modulus for PDMS is about five orders of magnitude smaller than that of metal wires. Therefore, optical waveguides even much thicker than the metal wires typically used for this application will be extremely flexible and capable of reducing the tethering forces by some orders of magnitude. In addition, optical communication has a much wider bandwidth than electromagnetic method of signal telemetry.

This Example reports on the efficiency of an optical waveguide in collecting light energy transcutaneously in human subjects and the attenuation of light intensity along its length.

Methods:

Participants:

Healthy subjects with the age of greater than 18 years were recruited following the guidelines approved by the New Jersey Institute of Technology Institutional Review Board ("IRB"). Subjects with a history of malignancy, as well as people who had scar or wound on the hand skin were excluded. All subjects wore laser safety goggles during data collection. All participants reported their age, gender, weight and height. Body mass index ("BMI") was calculated using weight/height$^2$ formula.

Thirteen volunteers with an average age of 29.6 plus/minus 7.1 (mean plus/minus std.) met the inclusion criteria and enrolled in this study. In this group, the frequency of gender was 3=Female, 10=Male; the BMI was distributed as 1=underweight, 7=normal, 5=overweight; the distribution of skin color was 3=pale white/white, 7=cream white/moderate brown, 3=dark brown/dark. The skin colors of subjects were grouped into 3 categories following the Fitzpatrick scale: I—Type 1 & 2 (pale white, white), II—Type 3 & 4 (cream white, moderate brown) and III—Type 5 & 6 (dark brown, darkest brown) based on observation of the human skin pigmentation.

PDMS-Based Optical Waveguide Fabrication:

Dow Corning Sylgard 184 and OE-6550 silicon elastomers were used to fabricate two-layered core-cladding PDMS optical structure with different refractive indices for confinement of light. The core was fabricated with OE-6550 which had relatively higher refractive index (RI=1.55) than Sylgard 184 (RI=1.41), the cladding material.

The fabrication of PDMS core began by mixing a curing agent (OE-6550A) with PDMS liquid prepolymer (OE-6550B) for about 15 minutes (ratio 1:1). After achieving a homogenous mixture, the solution was placed in a vacuum for 30 minutes to remove air bubbles that were trapped within the mixture. The PDMS solution was then poured in a 10 cc syringe. The mixture was injected into a 17 cm Teflon tubing (0.8 mm ID, McMaster) using a 19 gauge needle. Once the tubing was filled with OE-6550, it was baked at 60° C. for 8 hours. Then the tubing was stripped from the cured core by making a cut at one end and pulling apart.

The cladding mixture was prepared following similar steps using Slygard 184A/B liquid prepolymer (mixing ratio 10:1). The core prepared earlier was held by a fine tip forceps and dipped into the cladding mixture, gently pulled up and then hung inside the oven to be cured vertically at 80° C. for 2 hours. The cladding had a thickness of approximately 300 μm plus/minus 50 μm. The attenuation measurements were made with the waveguides that turned out to have a total diameter of 1.1 plus/minus 0.05 mm.

Measurements of Optical Attenuation:

To determine the attenuation loss per unit length of the fabricated cylindrical waveguides, the cutback method was employed. A 15-cm waveguide was coupled to a red laser diode (635 nm, 4.9 mW, Thorlabs) and the light exiting from the other end was collected with a photodiode (Silicon Photodiode, 10 mm×10 mm active area, Thorlabs) for measurements of attenuation in straight positioning. Light intensity measurements were taken for waveguide lengths of 15 cm to 5 cm by progressively cutting off 5 mm lengths of the waveguide. The voltage output from the photodiode array was converted to a light power value using the photodiode responsivity (0.72 A/W) provided by the manufacturer. The total attenuation was determined using:

$$A = -10 \log(P_{out}/P_{in}) \quad \text{(Equation 1)}$$

where A is the attenuation in decibels (dB), $P_{in}$ is the power injected into the waveguide, $P_{out}$ is the power measured by the photodiode array. The results were plotted as a function of waveguide length to determine the total attenuation per unit length (dB/cm).

Light Transmission Though the Skin:

The skin flap (thenar web space) between the thumb and the index finger in both hands were cleaned using 70% ethanol to remove residues that could affect light measurements. The setup consisted of a semiconductor laser module (650 nm, 4.9 mW, Flexpoint, Uberlingen, Germany) as a light source and a photodiode (FDS 1010-CAL, 10 mm×10 mm active area, Thorlabs, USA) as a detector. The diameter of the collimated light beam was set to Ø1.1 mm by passing it through a pinhole and aligned with the Ø1.1 mm waveguide on the other side of the hand (FIG. 11).

Figure 11:
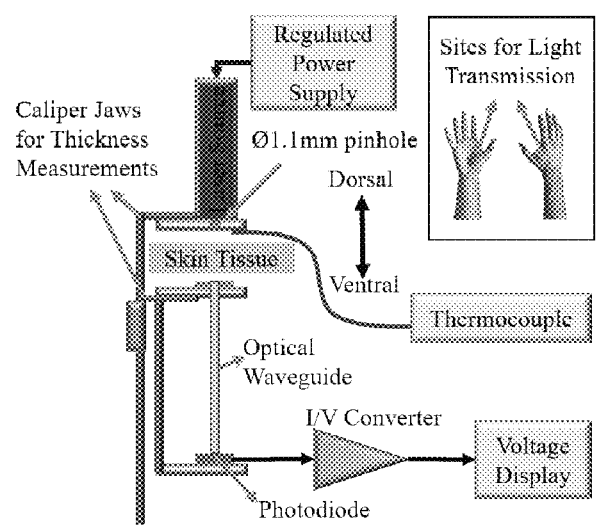
FIG. 11 shows an experimental setup for light collection through the hand skin; Inset: representative image of right hand showing the point of measurement near beginning of arrows.

A commercial caliper was utilized to hold the light source and 5 cm long waveguide in alignment (FIG. 11). The subject's hand was placed between the caliper jaws facing down and tightened gently to make a good skin contact while being careful not to compromise the blood circulation. The thickness of the skin was recorded as well as the light power ($P_{out}$) exiting on the ventral site of the thenar skin flap.

The local skin temperature was measured by a T-Type thermocouple sandwiched between the laser source and the skin, after allowing the temperature to stabilize for 5 seconds.

Figure 12:
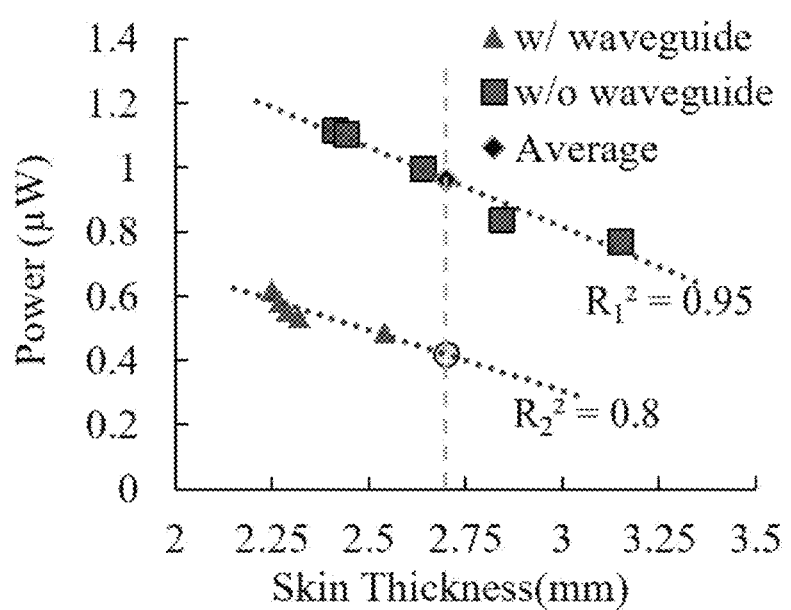
FIG. 12 shows a representative plot for determination of percent transmission in the left hand of subject 10; Top dot on dotted vertical line: average value of 5 measurements without the waveguide, bottom dot on dotted vertical line: measurement with the waveguide at the same skin thickness calculated by extrapolation.

Data Analysis:

Five measurements were taken from each hand first with the photodiode placed adjacent to the skin on the ventral side without the optical waveguide. These measurements were averaged as a representative amount of light transmitted through an average skin thickness for this particular hand (top diamond on vertical dotted line in FIG. 12). Multiple-point measurement was seen as necessary to eliminate outliers due to misplacement of the caliper across very thin or thick areas of the thenar skin. Five more measurements were made in the same hand with the waveguide inserted between the hand and the photodiode as shown in FIG. 11. A linear line was fit to the measurements and the transmission at the same skin thickness that was found as the average thickness without the waveguide was calculated by interpolation/extrapolation (bottom circle on vertical dotted line in FIG. 12). The ratio of the light transmission at the same skin thickness with and without the waveguide (bottom circle/top diamond) was taken as the attenuation due to the waveguide, which in fact consisted of two parts. First, photons enter the optical waveguide in a very wide range of angles after passing through a scattering medium, such as the human skin. Most of those photons cannot be contained in the waveguide because of the large angle of entry. Second, light is attenuated along the waveguide due to absorption. One could factor out the latter by measuring this value separately with a collimated laser beam. The net result was the light collection efficiency of the waveguide at the interface with the skin.

Figure 13:
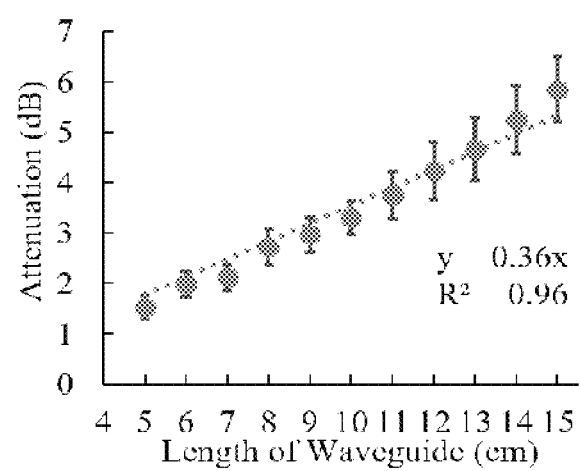
FIG. 13 shows average attenuation of five cylindrical waveguides as a function of waveguide length; Error bars: one-standard deviation; dashed-line: linear fit.

Results:

Attenuation in the PDMS Waveguide:

The cylindrical optical waveguide had a good confinement of red light (λ=635 nm) and relatively low attenuation of approximately 0.36 plus/minus 0.03 dB/cm (mean plus/minus std, n=5, $R^2$=0.96) in straight positioning (FIG. 13).

Figure 14:
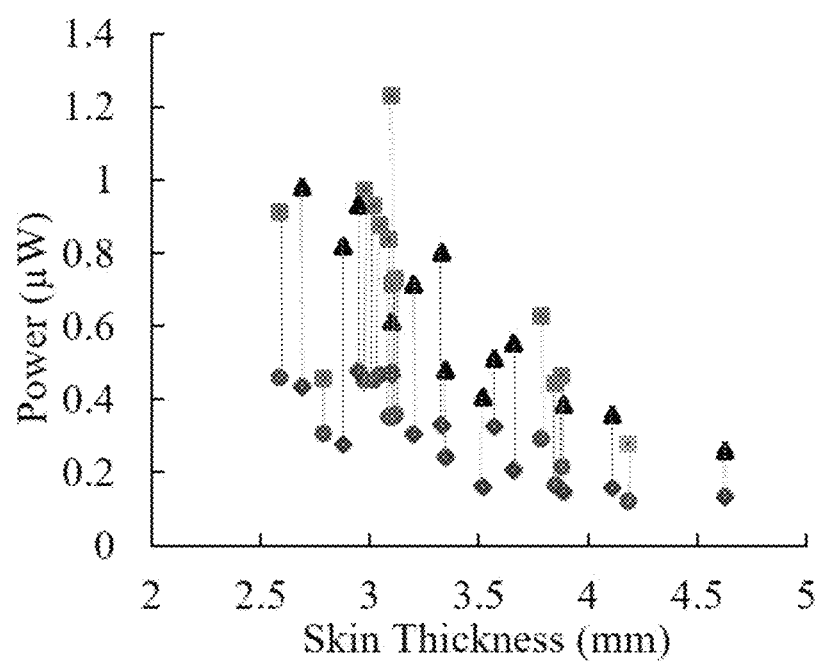
FIG. 14 shows a comparison plot to show the difference between the values of measurements with waveguide (circles and diamonds) and hand alone (squares and triangles) as a function of thickness (52 data points from left and right hands of 13 subjects); Each vertical dash line represents the pair from the same hand.

Transmission through the Hand Skin:

The incident light intensity on the skin was 374 µW, as measured after the pinhole. The light intensity that was transmitted through the skin and received by a Ø1.1 mm circular photodiode area ranged between 0.3 µW to 1.0 µW in different subjects while the skin thickness varied from 4.6 mm to 2.6 mm (squares in FIG. 14). This substantial attenuation of light intensity is mostly due to scattering of photons inside the tissue. The circles in FIG. 14 show the light intensities collected with the waveguide (also Ø1.1 mm), rather than the photodiode, after factoring out the attenuation along the waveguide that was shown in FIG. 13. Thus, the ratio of the circles-diamonds over the squares-triangles in FIG. 14 in each hand gives the light collection efficiency of the waveguide in each case. The light collection efficiency averaged across all subjects (both hands) was 44 plus/minus 11% (mean plus/minus std).

Temperature Elevation of the Skin:

The local hand temperature in each subject was maintained during data collection due to low power illumination. The maximum change detected was 0.1° C., which is considered within the body maintaining temperature.

Discussion:

One purpose of this study was to measure the light collection efficiency of PDMS-based optical waveguides across the human skin. An experimental setup was designed to determine how much of the laser energy could be collected by the waveguide and transmitted to a photodiode after having been scattered passing through the skin. The electrical power generated at the photodiode may then be utilized to power an implantable microelectrode array in order to avoid wire interconnections. There are some important factors such as pigmentation and the thickness of various skin layers that directly effects the light absorption and scattering inside the tissue. However, based on the data presented, the transmission efficiency of optical waveguides is not significantly affected by the gender, the BMI, or skin pigmentation (p greater than 0.5 for all groups).

The location on hands that were used for measurements included a layer of dermis between two layers of epidermis on each side. Because a small pinhole was used to collimate the beam, the incident power (375 µW) was only a small fraction of what comes out of the laser source. The incident light beam was substantially attenuated also by the skin (300-500 times) at varying amounts depending on the thickness of the thenar skin in different subjects. The thenar skin flap was chosen for convenience in this study. The skin thickness varies greatly around the body and the total transmitted light power will change depending on the site. The total power collected by the waveguide will also be a function of its diameter and the attenuation along its length. With the collection efficiencies and the attenuations that are reported here, one can estimate the total power for different fiber diameters and lengths. Fabrication techniques can be improved to achieve particularly blemish free PDMS surfaces and thus obtain better containment of light inside the waveguide. However, such imperfections may become more influential when the waveguide is bent, twisted, or stretched, and the attenuation measurements reported here can be repeated under those conditions. But, the collection efficiency of the waveguide at the tissue-waveguide interface should be independent of the attenuation along its length.

Conclusion:

The results demonstrate that light energy could be collected transcutaneously and transmitted to a deeper location inside the neural tissue with high efficiencies using PDMS waveguides. Considering the maximum allowed light exposures per unit area on the human skin, this efficiency implies that significant levels of optical power can be transmitted to an implant without using metal wires that frequently break and cause the implant to fail. A PDMS waveguide would generate much smaller tether forces compared to metal wire interconnects. A trade-off exists between the size of the waveguide and the total power that can be delivered. A larger cross-sectional area of the waveguide would allow more optical power to be transmitted without exceeding the exposure limits on the skin surface, however, generating higher tethering forces potentially on the implant.

Although the systems/methods of the present disclosure have been described with reference to exemplary embodiments thereof, the present disclosure is not limited to such exemplary embodiments/implementations. Rather, the systems/methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

REFERENCES:

Abdo et al., Near-infrared light penetration profile in the rodent brain. J Biomed Opt, 2013. 18(7): p. 075001.

Ersen et al., Temperature elevation profile inside the rat brain induced by a laser beam. J Biomed Opt, 2014. 19(1): p. 15009.

Abdo et al., Temperature elevation inside neural tissue illuminated by NIR laser. in Engineering in Medicine and Biology Society, EMBC, 2011 Annual International Conference of the IEEE. 2011.

Yucel et al., FEA Modeling of Temperature Elevation in Neural Tissue Illuminated by a Laser: Transient Effects, in 6th Annual International IEEE EMBS Conference on Neural Engineering. 2013, IEEE: San Diego, Calif. p. 1112-1114.

Abdo et al, Intraspinal stimulation with light activated micro-stimulators. in Neural Engineering (NER), 2011 5th International IEEE/EMBS Conference on. 2011.

Abdo et al., Floating light-activated microelectrical stimulators tested in the rat spinal cord. J Neural Eng, 2011. 8(5): p. 056012.

Ersen, A., et al., Chronic tissue response to untethered microelectrode implants in the rat brain and spinal cord. J Neural Eng, 2015. 12(1): p. 016019.

Freedman, D. S., et al. Addressable floating light activated micro-electrical stimulators for wireless neuro stimulation. in Neural Engineering (NER), 2011 5th International IEEE/EMBS Conference on. 2011.

Leblebici, Y, Subthreshold Source-Coupled Circuit Design for Ultra-Low-Power Applications. in Distinguished Lecturer of the IEEE Circuits and Systems Society. 2010-2011.

Tajalli et al., Extreme low-power mixed signal IC design : subthreshold 5 source-coupled circuits. 2010, New York: Springer. xxxiii, 274 p.

Muller, P., et al., Design and Integration of All-Silicon Fiber-Optic Receivers for Multi-Gigabit Chip-to-Chip Links, in European Solid-State Circuits Conference. 2006:Montreux, Switzerland.

Unlu, M. S., et al., High-speed Si resonant cavity enhanced photodetectors and arrays. 10 Journal of Vacuum Science & Technology A: Vacuum, Surfaces, and Films, 2004. 22(3): p. 781-787.

Koklu, G., et al., Characterization of standard CMOS compatible photodiodes and pixels for Lab-on-Chip devices, in IEEE International Symposium on Circuits and Systems (ISCAS). 2013. p. 1075-1078.

What is claimed is:

1. An optical conduit assembly comprising:
    an optical conduit positioned in a first desired anatomical location, the optical conduit configured to wirelessly transmit optical energy to an implantable device positioned in a second desired anatomical location, the first desired anatomical location different and spaced apart from the second desired anatomical location with anatomical tissue positioned between the first desired anatomical location and the second desired anatomical location;
    a light source configured to deliver optical energy to the optical conduit;
    wherein after the light source delivers optical energy to the optical conduit, the optical conduit wirelessly transmits optical energy from the first desired anatomical location to the implantable device positioned at the second desired anatomical location, with the optical energy travelling through the anatomical tissue positioned between the first desired anatomical location and the second desired anatomical location.

2. The assembly of claim 1, wherein the optical conduit is a PDMS-based optical conduit.

3. The assembly of claim 1, wherein the implantable device is an untethered neural micro-stimulator or a neural prosthetic.

4. The assembly of claim 1, wherein the first desired anatomical location includes the epidermis, and wherein the second desired anatomical location is a deep location inside the body or brain.

5. The assembly of claim 1, wherein the light source is an external laser diode, the external laser diode positioned external to the first and second desired anatomical locations.

6. The assembly of claim 1, wherein the optical conduit includes an optical-to electrical converter attached to a distal tip of the optical conduit.

7. The assembly of claim 6, wherein the optical-to electrical converter is a photodiode.

8. The assembly of claim 1, wherein the optical conduit includes at least one curved section.

9. The assembly of claim 1, wherein the implantable device includes an optical-to electrical converter.

10. An optical conduit system comprising:
    a substrate having a plurality of holes, each hole housing an end of one respective optical conduit of a plurality of optical conduits, the substrate and the plurality of optical conduits positioned in a first desired anatomical location;
    a plurality of light sources, each light source configured to deliver optical energy to a respective optical conduit of the plurality of optical conduits;
    a plurality of implantable devices positioned in a second desired anatomical location, the first desired anatomical location different and spaced apart from the second desired anatomical location with anatomical tissue positioned between the first desired anatomical location and the second desired anatomical location;
    wherein after each light source delivers optical energy to its respective optical conduit of the plurality of optical conduits, each optical conduit wirelessly transmits optical energy from the first desired anatomical location to a respective implantable device of the plurality of implantable devices positioned at the second desired anatomical location, with the optical energy travelling through the anatomical tissue positioned between the first desired anatomical location and the second desired anatomical location.

11. An optical conduit system comprising:
    a substrate having a plurality of holes, each hole housing an end of one respective optical conduit of a plurality of optical conduits, the substrate and the plurality of optical conduits positioned in a first desired anatomical location;
    a plurality of light sources, each light source configured to deliver optical energy to a respective optical conduit of the plurality of optical conduits;
    a plurality of implantable devices positioned in a second desired anatomical location, the first desired anatomical location different and spaced apart from the second desired anatomical location with anatomical tissue positioned between the first desired anatomical location and the second desired anatomical location;
    wherein after each light source delivers optical energy to its respective optical conduit of the plurality of optical conduits, each optical conduit wirelessly transmits optical energy from the first desired anatomical location to a respective implantable device of the plurality of implantable devices positioned at the second desired anatomical location, with the optical energy travelling through the anatomical tissue positioned between the first desired anatomical location and the second desired anatomical location;
    wherein the first desired anatomical location includes the epidermis, and wherein the second desired anatomical location is a deep location inside the body or brain; and
    wherein each light source is an external laser diode, each external laser diode positioned external to the first and second desired anatomical locations.

12. The assembly of claim 11, wherein each optical conduit is a PDMS-based optical conduit.

13. The assembly of claim 11, wherein each implantable device is an untethered neural micro-stimulator or a neural prosthetic.

14. The assembly of claim 11, wherein each optical conduit includes an optical-to electrical converter attached to a distal tip of the optical conduit.

15. The assembly of claim 14, wherein each optical-to electrical converter is a photodiode.

16. The assembly of claim 11, wherein each optical conduit includes at least one curved section.

17. The assembly of claim 11, wherein each implantable device includes an optical-to electrical converter.

* * * * *